United States Patent [19]

Vollmer et al.

[11] Patent Number: 4,584,269

[45] Date of Patent: Apr. 22, 1986

[54] METHOD FOR STABILIZING THE ENZYMATIC ACTIVITY OF PHENYLALANINE AMMONIA LYASE DURING L-PHENYLALANINE PRODUCTION

[75] Inventors: Patricia J. Vollmer, Olney; Jeffrey J. Schruben, Rockville; John P. Montgomery, Clarksburg; Huei-Hsuing Yang, Rockville, all of Md.

[73] Assignee: Genex Corporation, Rockville, Md.

[21] Appl. No.: 547,258

[22] Filed: Oct. 31, 1983

[51] Int. Cl.$^4$ .................. C12P 13/22; C12N 9/88; C12N 9/96; C12R 1/645

[52] U.S. Cl. ............................ 435/108; 435/232; 435/801; 435/911; 435/188

[58] Field of Search .................. 435/108, 232, 801

[56] References Cited

FOREIGN PATENT DOCUMENTS 1489468 10/1977 United Kingdom .................. 101/8

OTHER PUBLICATIONS

L-Phenylalanine Ammonia-Lyase.II. Mechanism and Kinetic Properties of the Enzyme from Potato Tubers, Evelyn A. Havir & Kenneth R. Hanson, *Biochemistry*, vol. 7, No. 5, May, 1968.

Production of L-Phenylalanine from Trans-Cinnamic Acid with *Rhodotorula glutinis* Containing L-Phenylalanine Ammonia-Lyase Activity, *Applied and Environmental Microbiology*, Nov. 1981, Shigeki Yamada et al., vol. 42, pp. 773-778.

*Primary Examiner*—Lionel M. Shapiro
*Attorney, Agent, or Firm*—Bernard, Rothwell & Brown

[57] ABSTRACT

A method for the enzymatic conversion of t-cinnamic acid and ammonia to L-phenylalanine, using the catalyst, phenylalanine ammonia-lyase, wherein the stability and useful life of the enzyme are improved by conducting the conversion under substantially anaerobic, static conditions.

16 Claims, No Drawings

METHOD FOR STABILIZING THE ENZYMATIC ACTIVITY OF PHENYLALANINE AMMONIA LYASE DURING L-PHENYLALANINE PRODUCTION

BACKGROUND OF THE INVENTION

Enzymatic methods using L-phenylalanine ammonia-lyase for the conversion of trans-cinnamic acid to L-phenylalanine generally comprise the steps of (a) aerobically propagating a phenylalanine ammonia-lyase (hereinafter PAL)-producing microorganism in an aqueous nutrient medium until substantial amounts of PAL are produced, (b) contacting the cells of the PAL-producing microorganism from step (a), either as the whole culture broth or separated cells therefrom, or the isolated enzyme, with ammonium ions and trans-cinnamate ions and allowing the reaction to proceed under controlled temperature and pH conditions until the conversion to L-phenylalanine is substantially complete and (c) separating and recovering the L-phenylalanine from the reaction mixture.

The foregoing method is described, for example, in British Patent No. 1,489,468 (Oct. 19, 1977). A drawback to the use of this process for commercial production has been the relative instability of PAL, and its inhibition by the substrate, t-cinnamic acid. To drive the reaction toward the production of L-phenylalanine and to counteract the effects of substrate inhibition, the above-mentioned British patent describes a process which employs large masses of PAL-containing cells and excess concentrations of ammonium ions.

Yamada, S. et al. (*Appl. and Environ. Microbiol.*, 42, 7873-778 (1981)) have described the production of L-phenylalanine from t-cinnamic acid using PAL-containing *Rhodotorula glutinis* cells. They speculated that the lack of previous practical application of this process was attributable to the low activity and instability of microbial PAL. Yamada, et al. found that L-isoleucine had a stabilizing effect on PAL, and extended the useful period of activity of the enzyme. These authors further observed the inhibitive effect of the substrate, noting that at practical concentrations of t-cinnamic acid (150 mM), the rate of conversion of L-phenylalanine was reduced to one-half the maximum rate.

Despite the improvements described above, as far as is known, the PAL process has not been used for the commercial production of L-phenylalanine. The instability and low activity of the enzyme have continued to be disadvantages of this process.

SUMMARY OF THE INVENTION

In accordance with the present invention, an improved process for producing L-phenylalanine involves:
(a) cultivating a PAL-producing microorganism under aerobic, growth-promoting conditions;
(b) inducing the cells produced by step (a) to make to make PAL under PAL-producing conditions;
(c) subjecting the PAL-containing cells from step (b) to substantially anaerobic, static conditions to maintain the PAL activity;
(d) combining the PAL produced by step (b) with t-cinnamic acid and ammonium ions under substantially anaerobic, static L-phenylalanine-producing conditions to produce L-phenylalanine; and
(e) recovering the L-phenylalanine so produced.

It has been found that the catalytic activity of microbially produced phenylalanine ammonia-lyase can be stabilized by maintaining a reduced concentration of oxygen in the fermentation medium after PAL production.

DESCRIPTION OF THE INVENTION

In the practice of this invention, the process of making L-phenylalanine by reacting trans-cinnamic acid and ammonia in the presence of L-phenylalanine ammonia-lyase has been improved, such that higher yields of L-phenylalanine are obtained and a high degree of the catalytic activity of the PAL can be maintained throughout the reaction.

This improvement involves conducting the enzymatic conversion reaction under substantially anaerobic, static conditions. These conditions have been found to significantly stabilize the PAL activity over the course of the reaction, thus enhancing conversion rates and yields. The exact mechanisms of this stabilizing effect are not known; however, it is believed that the chemical effects of oxygen and the mechanical effects of agitation operate independently to deteriorate the activity of the enzyme. Therefore, minimizing these effects tends to prolong the useful life of the enzyme.

Anaerobic conditions may be achieved by various means, such as sparging with an inert gas (e.g., nitrogen), reducing or eliminating agitation, and limiting any air headspace over the surface of the cell-containing medium. Two or more of these techniques may advantageously be combined.

Static conditions are achieved by reducing agitation of the conversion reaction mixture to a minimal level sufficient to maintain substantial homogeneity. Some agitation is generally desired, particularly with whole-cell reactions, to prevent settling of solids or solid-bound reaction components.

The PAL-producing microorganisms employed in the method of this invention require oxygen for growth; therefore, the cells are initially cultivated under aerobic, growth-promoting conditions. Generally, conventional procedures are employed for growing the cells. Cells are inoculated into a nutritional medium containing assimilable sources of carbon and nitrogen and essential vitamins, minerals and other growth factors. Suitable carbon sources can include various refined or crude carbohydrates such as glucose, sucrose, molasses, starches, grains and the like. A preferred carbon source is glucose. Nitrogen sources include inorganic ammonium salts, such as ammonium phosphate, ammonium sulfate, ammonium acetate, ammonium citrate, ammonium nitrate and the like and organic nitrogeneous substances such as soybean meal, meat infusions, amino acids, corn steep liquor, protein hydrolyzates, peptone, yeast extracts, and the like. A preferred nitrogen source for the process of this invention is yeast extract, and this nutrient may advantageously be combined with diammonium phosphate which supplies both nitrogen and phosphorous.

Vitamins, minerals and other growth factors may be supplied by the carbon and nitrogen sources (e.g., via the yeast extract) or may be supplied separately. These components can vary with the particular microorganism employed. Typically, trace minerals such as zinc, manganese, iron, cobalt, and calcium can be supplied in growth-promoting amounts as inorganic salts. These minerals may, for example, be supplied with process water, e.g., tap water, sea water, etc. Nutrient media of the type described are well known, and can vary in composition widely.

After growing the cells to the desired cell density under aerobic conditions, they are induced to make PAL under aerobic, PAL-producing conditions. PAL induction is generally achieved by adding small amounts of a compound that acts as a substrate for the PAL. L-Phenylalanine is a good PAL inducer, and a number of analogs of L-phenylalanine also induce the synthesis of this enzyme. For example, D,L-phenylalanine, L-tyrosine, and D,L-tyrosine can be employed for this purpose. In addition, it has been discovered that various crude nitrogen sources can be used for PAL induction. Such crude nitrogen sources include hydrolyzed proteins which contain substantial amounts of L-phenylalanine or L-tyrosine. Casein and blood hydrolyzates can advantageously be used as crude nitrogen sources for the induction of PAL synthesis.

The PAL inducer is added to the cells in a PAL-inducing amount, which generally ranges from about 0.1 to 10 g/l of the fermentation medium. Preferably, the PAL inducer is employed at a concentration from about 4 to about 8 g/l of the fermentation medium. During this step, PAL-inducing conditions of temperature and pH, aeration and agitation are maintained. The temperature and pH are generally maintained within physiologically compatible limits during PAL induction. Somewhat reduced temperatures, e.g. from about 15° C. to about 25° C. are preferred, because at these lower temperatures, enzyme stability is improved and the rate of consumption of the PAL inducer is decreased. A preferred pH for the PAL induction ranges from about 5.5 to about 7.5, where relatively higher PAL levels are achieved.

If the cells employed are sensitive to catabolic repression of PAL synthesis, then, prior to induction, means should be employed to reduce or eliminate catabolites and their precursors from the medium. This may be accomplished by separating cells from the medium, washing them and suspending them in a catabolite-free medium. Alternatively, the cells can be allowed to grow until the nutrients are substantially exhausted before the PAL induction procedure is initiated.

The cells are advantageously cultivated under PAL-inducing conditions until the PAL activity reaches at least about 0.5 units per ml, preferably at least about 2.0 units per ml. A unit of PAL activity is defined as the amount of enzyme which catalyzes the formation of 0.83 $\mu$mole of t-cinnamic acid per minute at 22° C. or 1 $\mu$mole per minute at 30° C. It has been observed that under these conditions, the PAL activity increases to a certain point and then begins to diminish. PAL produced by these procedures may be employed to produce L-phenylalanine from t-cinnamic acid and ammonia. These reactants can be added directly to the PAL-containing cells in an aqueous medium, or the cells or enzyme isolated therefrom can be immobilized by known procedures on a solid support that can be reused for so long as the enzyme activity is maintained.

L-Phenylalanine is produced by this method under L-phenylalanine-producing conditions. These conditions will vary, depending upon the particular microbial strains employed, whether whole cells or cell-free enzyme preparations are used and whether immobilized systems are employed. In general, t-cinnamic acid and aqueous ammonia (or soluble ammonium salts) are supplied in amounts such that the ammonia is substantially in excess of the t-cinnamic acid on a molar basis. The t-cinnamic acid is employed in amounts of from about 5 to about 25 g/l, preferably from about 10 to about 20 g/l of the reaction mixture. At these t-cinnamic acid concentrations, the ammonia concentration generally ranges from about 0.1 to about 9.0 molar, preferably from about 5.0 to about 8.0 molar. The PAL-catalyzed reaction of t-cinnamic acid and ammonia to produce L-phenylalanine is reversible, and in fact, the equilibrium favors the breakdown of L-phenylalanine. Therefore, to establish a favorable reaction rate, the t-cinnamic acid concentration in the reaction mixture is advantageously maintained at a relatively high level. On the other hand, excessively high concentrations of t-cinnamic acid can inhibit the activity of PAL. Accordingly, a preferred procedure of this invention involves periodically or continuously feeding t-cinnamic acid into the reaction mixture during all but the latter stage of the reaction to maintain the concentration of this reactant within the ranges referred to above. Temperature during L-phenylalanine production is generally maintained within physiologically acceptable limits. The temperature preferably ranges from about 10° C. to about 30° C., most preferably from about 14° C. to about 24° C. These lower reaction temperatures have been found to prolong enzyme stability, without deleteriously affecting reaction rates. L-phenylalanine-producing conditions also include an alkaline pH, which generally can range from about 9 to about 11, preferably from about 10.4 to about 10.8.

Preferred ammonium salts are those which contain no halogen ions. The presence of halogens in the substrate solution has been found to inhibit the catalytic activity of PAL. Therefore, preferred ammonium salts include ammonium carbonate, ammonium sulfate, ammonium nitrate, ammonium citrate, ammonium acetate, and ammonium phosphate. An especially preferred ammonium salt is ammonium carbonate. A convenient procedure for preparing a substrate solution is to dissolve the t-cinnamic acid in an aqueous ammonia solution, and then adjust the pH of the solution as desired by sparging with carbon dioxide or adding a mineral acid, such as sulfuric acid.

The enzymatic conversion of t-cinnamic acid and ammonia to L-phenylalanine is preferably conducted in a bioreactor vessel. This procedure advantageously involves separating the cells from their fermentation medium by filtration or centrifugation and suspending them in the substrate solution of t-cinnamic acid and ammonium ions. This solution is sparged with an inert gas, such as nitrogen, to displace dissolved oxygen, and is maintained in a substantially static condition.

As indicated above, phenylalanine ammonia-lyase has been found to be quite sensitive to degradation in the presence of oxygen and under the influence of agitation. Whereas agitation in conventional reaction vessels (e.g. deep tank fermentors) is conducted at a power level of from about 0.5 to 5 watts per liter, agitation power input for reaction mixtures of the present invention advantageously averages, over the course of the reaction, below about 500 milliwatts per liter, preferably below about 100 milliwatts per liter. Higher levels of power input, for example, up to about 5 watts per liter, can be used, but in such cases, the agitation is applied intermittently, e.g., 30 seconds of mixing at intervals of 2 hours.

The nature of the agitation can also affect enzyme stability. A low shear mixing is preferred. This type of agitation can be conveniently provided by periodically sparging the reaction mixture with an inert gas, such as nitrogen. In addition, mechanical agitators designed for low shear mixing can be employed. Generally, only enough agitation is employed to maintain a substantially homogeneous mixture during the course of the reaction.

The bioreaction is continued until substantial amounts of L-phenylalanine have accumulated in the reaction mixture. Generally recovery procedures are initiated when the L-phenylalanine concentrations reach about 30 g/l, preferably about 45-50 g/l. L-Phenylalanine can be recovered from the reaction mixture by any suitable means. For example, solids can be removed by filtration or centrifugation to produce a clarified solution, and L-phenylalanine can be precipitated from that solution by adjusting the pH to the isoelectric point of L-phenylalanine, i.e., about 5.5.

The following examples further illustrate the present invention, and demonstrate the beneficial effects of employing anaerobic reaction conditions and reducing agitation on the stability and useful life of the PAL enzyme. These examples are not to be construed as limiting the present invention.

EXAMPLE I

To determine the effect of pH on the production of L-phenylalanine, *Rhodotorula rubra* cells assayed at 51 units of PAL activity per gram dry cell weight (dcw) were used for laboratory scale reactions of t-cinnamic acid and ammonia. The tests were performed with 4 g/l dcw at 25° C. The substrates were 15 g/l cinnamate, 100 g/l (NH$_4$)$_2$ SO$_4$, pH of from 9.4 to 10.6 obtained by adjusting with NH$_4$OH. The results of this experiment, shown in Table 1, demonstrate that the maximum conversion rate was at pH 10.6. It was also observed that at pH's of 10.6 and above, PAL activities began to diminish.

EXAMPLE II

The effects of agitation and air (oxygen supply) on PAL activity were determined by a comparative conversion reaction to produce L-phenylalanine using 2 and 4 g/l dcw at 25° C. and pH 10.3 or 9.4. The results of these experiments are shown in Table 2. Efficacy of the catalyst was enhanced in unagitated reaction vessels in which oxygen was eliminated by completely filling the reactor vessel, or by purging with nitrogen or bubbling with nitrogen to maintain an inert atmosphere within the reaction vessel.

EXAMPLE III

L-phenylalanine production from cinnamic acid and ammonia was carried out in a bioreactor, using whole cells of *Rhodotorula rubra* having high PAL enzyme activity. To 390 liters of water was added 11.2 kg of trans-cinnamic acid, followed by 470 liters of 29% ammonia water. After the cinnamic acid was dissolved, the pH of the solution was adjusted to 10.6 by addition of 31 kg of carbon dioxide. The solution was de-aerated by sparging with nitrogen gas for 5 minutes. 5.06 kg (dry weight) of *Rhodotorula rubra* cells were added to the substrate solution, and the reaction was allowed to proceed for 130 hours. Additional substrate was periodically added to the bioreactor in the form of a concentrated ammonium cinnamate solution. After each addition, the contents of the bioreactor were briefly mixed by sparging with nitrogen gas. Temperature in the bioreactor was maintained at 29° C. during the first 17 hours of incubation, then decreased gradually until 13° C. was reached at 130 hours.

After 130 hours of incubation, the substrate solution contained 42.7 g/l of L-phenylalanine, and 6.4 g/l of trans-cinnamic acid.

The cells were separated from the substrate solution by means of a disc-bowl centrifuge. The supernatant from the centrifuge was filtered, and ammonia and ammonium carbonate removed by evaporation. Upon cooling, L-phenylalanine crystals precipitated. The L-phenylalanine crystals were collected in a basket centrifuge, rinsed with cold water, and dried. 22 kg of L-phenylalanine was recovered.

TABLE 1

| Run | dcw (g/l) | Temp °C. | pH | Phenylalanine (After 1 hour of reacting) mole/min/g DCW |
|---|---|---|---|---|
| 1 | 4 | 25° | 9.4 | 2.45 |
| 2 | 4 | 25° | 9.7 | 3.73 |
| 3 | 4 | 25° | 10.0 | 5.60 |
| 4 | 4 | 25° | 10.3 | 6.50 |
| 5 | 4 | 25° | 10.6 | 7.00 |

TABLE 2

| Run | dcw (g/l) | Agitation (+ or −) | Atmosphere Air/N2 | L-Phe Produced (g/l) 2 hr | 8 hr | 24 hr | 42 hr |
|---|---|---|---|---|---|---|---|
| 1 | 2 | + | Air | .41 | 1.0 | 1.9 | 1.8 |
| 2 | 2 | + | * | .40 | 1.3 | 2.9 | 3.1 |
| 3 | 2 | + | N | .41 | 1.3 | 2.2 | 2.2 |
| 4 | 2 | − | Air | .47 | 1.2 | 3.2 | 5.1 |
| 5 | 2 | − | * | .47 | 1.3 | 3.4 | 5.8 |
| 6 | 2 | − | N | .50 | 1.3 | 3.4 | 5.6 |
| 7 | 4 | − | Air | .64 | 2.0 | 5.1 | 7.2 |
| 8** | 4 | − | Air | .29 | 1.0 | 3.3 | 5.0 |
| 9** | 2 | − | Air | .15 | .53 | 1.7 | 2.2 |

*reactor vessel full to top
**pH 9.4

We claim:

1. A method for producing L-phenylalanine which comprises:
   (a) combining phenylallanine ammonia-lyase with t-cinnamate and ammonium ions under substantially anaerobic, static L-phenylalanine-producing conditions to produce L-phenylalanine; and
   (b) recovering the L-phenylalanine so produced.

2. The method of claim 1, in which the anaerobic conditions of steps (c) and (d) are at least partially achieved by sparging the medium which contains the PAL-containing cells with an inert gas.

3. The method of claim 1, wherein the substantially static conditions of steps (c) and (d) are achieved by periodically sparging the medium which cntains the PAL-containing cells with an inert gas.

4. The method of claim 1, wherein the substantially static conditions of steps (c) and (d) are achieved by a low level of mechanical agitation using a low shear agitator.

5. The method of claim 3 or 4, wherein the agitation power input averages, over the course of the reaction, less than about 500 milliwatts per liter of medium.

6. The method of claim 5, wherein the agitation power input averages, over the course of the reaction, less than about 100 milliwatts per liter of medium.

7. The method of claim 5, wherein, in step (d) the L-phenylalanine-producing conditions include a t-cinnamic acid concentration of from about 5 to about 25 g/l and an ammonia concentration of from about 0.1 to about 9.0 molar.

8. The method of claim 5, wherein, in step (d) the L-phenylalanine-producing conditions include a t-cinnamic acid concentration of from about 10 to about 20 g/l and an ammonia concentration of from about 5.0 to about 8.0 molar.

9. The method of claim 7, wherein the t-cinnamic acid concentration is maintained within the range of from about 5 to about 25 g/l during all but the latter stage of the reaction by periodically or continuously feeding t-cinnamic acid into the reaction mixture.

10. The method of claim 7, wherein the L-phenylalanine-producing conditions further include a reaction temperature of from about 10° C. to about 30° C. and a pH of from about 9 to about 11.

11. The method of claim 7, wherein the L-phenylalanine-producing conditions further include a reaction temperature of from about 14° C. to about 24° C., and a pH of from about 10.4 to about 10.8.

12. A method for producing L-phenylalanine which comprises:
   (a) cultivating a PAL-producing microorganism of the genus Rhodotorula under aerobic growth-promoting conditions;
   (b) inducing the cells produced in step (a) to make PAL under PAL-producing conditions;
   (c) subjecting the PAL-containing cells from step (b) to substantially anaerobic, static conditions to maintain the PAL activity;
   (d) combining the PAL produced in step (b) with t-cinnamate and ammonium ions under substantially anaerobic, static L-phenylalanine-producing conditions to produce L-phenylalanine; and
   (e) recovering the L-phenylalanine so produced.

13. The method of claim 10, wherein said microorganism is of the species Rhodotorula ruba.

14. The method of claim 12, wherein, in step (b), the cells are induced to make PAL by adding a PAL-inducing amount of a PAL-inducer selected from the group consisting of L-phenylalanine, D,L-phenylalanine, L-tyrosine, D,L-tyrosine and a hydrolyzed protein which contains substantial amounts of L-phenylalanine or L-tyrosine.

15. The method of claim 1, wherein the PAL-producing conditions include a temperature of from about 15° C. to about 25° C. and a pH of about 5.5 to about 7.5.

16. The method of claim 12, wherein the PAL-producing conditions further include substantially no catabolites in the cell medium during PAL induction.

* * * * *